US009689794B2

(12) United States Patent
Iwabuchi et al.

(10) Patent No.: US 9,689,794 B2
(45) Date of Patent: Jun. 27, 2017

(54) LITHIUM MEASUREMENT METHOD

(71) Applicant: METALLOGENICS CO., LTD., Chiba, Chiba (JP)

(72) Inventors: Takuya Iwabuchi, Chiba (JP); Tsugikatsu Odashima, Ichinoseki (JP); Hiroko Suzuki, Chiba (JP)

(73) Assignee: METALLOGENICS Co., Ltd, Chiba (JP)

( * ) Notice: Subject to any disclaimer, the term of this patent is extended or adjusted under 35 U.S.C. 154(b) by 0 days.

(21) Appl. No.: 14/439,298

(22) PCT Filed: Dec. 7, 2012

(86) PCT No.: PCT/JP2012/081742
§ 371 (c)(1),
(2) Date: Apr. 29, 2015

(87) PCT Pub. No.: WO2014/073119
PCT Pub. Date: May 15, 2014

(65) Prior Publication Data
US 2015/0276583 A1    Oct. 1, 2015

(30) Foreign Application Priority Data

Nov. 7, 2012    (JP) .................. 2012-245766

(51) Int. Cl.
*G01N 21/25* (2006.01)
*G01N 31/22* (2006.01)
*G01N 33/15* (2006.01)

(52) U.S. Cl.
CPC ............. *G01N 21/25* (2013.01); *G01N 31/22* (2013.01); *G01N 33/15* (2013.01)

(58) Field of Classification Search
CPC ..................................................... G01N 21/25

USPC ............................................... 436/79; 422/51
See application file for complete search history.

(56) References Cited

U.S. PATENT DOCUMENTS 7,241,623 B2 * 7/2007 Balazs .................. G01N 33/84
422/430

FOREIGN PATENT DOCUMENTS

JP    2006-43694 A    2/2006

OTHER PUBLICATIONS

Kenji Koyanagi, et al. Bunseki Kagaku vol. 51, No. 9, pp. 803-807 (2002).*
Kenji Koyanagi, et al. Bunseki Kagaku vol. 51, No. 9, pp. 803-807 (2002) translation obtained Jan. 13, 2016.*
Haiping Sun, Masaaki Tabata. Talanta 49 (1999) 603-610.*
Kenji Koyanagi, et al., "Synthesis of F28 tetraphenylporphyrin and its application to the separation and detection of lithium (I)", The Japan Society for Analytical Chemistry, Bunseki Kagaku, 2002, pp. 803-807, vol. 51, No. 9.
International Search Report of PCT/JP2012/081742, dated Jan. 15, 2013. [PCT/ISA/210].

* cited by examiner

*Primary Examiner* — Christine T Mui
*Assistant Examiner* — Emily Berkeley
(74) *Attorney, Agent, or Firm* — Sughrue Mion, PLLC

(57) ABSTRACT

To provide to a method for measuring and examining lithium ions in an aqueous solution of a specimen such as biomaterials or environment samples, by using a lithium reagent composition as a coloration reaction reagent and by visual observing or a simple a colorimeter. The lithium ions measuring method is characterized by contacting the specimen including serum and plasma test sample with an aqueous solution of a lithium reagent composition comprising a tetraphenyl porphyrin compound, a pH regulator and a pH buffer, by irradiating or expose the resulting solution with white light, and by detecting change in color tone by a visual observation or by detecting the sensitivity by a colorimeter.

(Continued)

Schematic diagram of a measuring apparatus according to the present invention

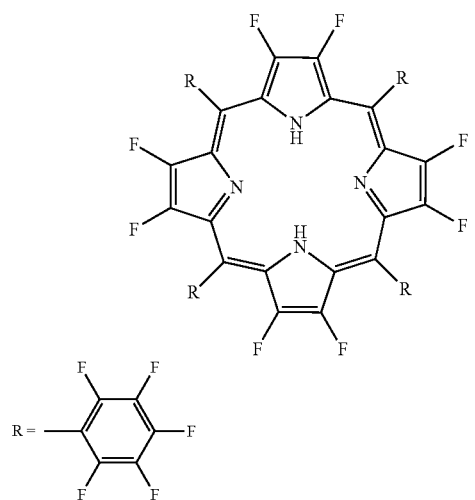
5 Claims, 7 Drawing Sheets

| 3 mM lithium sample base | | 1 time | 5 times | 10 times |
|---|---|---|---|---|
| Concentration of chelating reagent necessary to the final Li concentration at reaction | mM | 0.02 | 0.1 | 0.2 |
| Concentration of chelating reagent in the lithium reagent composition | mM<br>g/L | 0.08<br>0.1 | 0.38<br>0.4 | 0.75<br>0.8 |

1 mg/dL ≒ 1.44 mM

Change in spectrum of
F28 tetraphenylporphyrin complex formation

Table 1
Comparison of measured values obtained
by automatic analysis for control serum
unit : mM

| Control serum | Guaranteed value | Measured value obtained by the present invention |
|---|---|---|
| Prechnom U | 0.82 | 0.83 |
| Prechipass U | 2.30 | 2.20 |
| Pasonorm | 1.51 | 1.50 |
| Automom | 1.00 | 0.99 |

Fig. 7

[Table 2]

Correction method of this invention by subwavelength
of measured balues of hemolysis haemoglobin

|  |  | No hemolysis | Concentration of hemolysis haemoglobin (mg/dL) | | | |
|---|---|---|---|---|---|---|
|  |  |  | 250 | 500 | 750 | 1,000 |
| Measured lithium value (mM) | main wavelength only | 1.51 | 1.59 | 1.66 | 1.71 | 1.89 |
|  | correction with subwavelength | 1.51 | 1.51 | 1.53 | 1.51 | 1.54 |
| Recovery (%) | main wavelength only | 100 | 105 | 110 | 113 | 125 |
|  | correction with subwavelength | 100 | 100 | 101 | 100 | 102 |

Fig. 8

[Table 3]

Correct answer rate of lithium level
in control serum by prior arts (N=25 persons)

| Color Tone Reference (Standard Sample) | | Coloration |
|---|---|---|
| 0.6 mM ~ 1.5 mM | Control region | Yellow |
| 1.5 mM ~ 2.5 mM | Semipoisoning region | Orange |
| 2.5 mM ~ 3.5 mM | Poisioning region | Vermilion |
| 3.5 mM or higher | Dangerous region | Red |

| Control serum specimen (sample) | | | Coloration | Number of right answer | Correct answer rate |
|---|---|---|---|---|---|
| Autonorm | 1 mM | Control region | Yellow | 25 | 100% |
| Pathonorm | 1.6 mM | Semipoisoning region | Orange | 13 | 52% |
| Precinorm | 2.5 mM | Poisioning region | Vermilion | 13 | 52% |
| Model serum | 3.5 mM | Dangerous region | Red | 25 | 100% |

Fig. 9

[Table 4]

Correct answer rate of lithium level
in control serum by the present invention (N=25 persons)

| Color Tone Reference | (Standard Sample) | Coloration |
|---|---|---|
| 0.6 mM~1.5 mM | Control region | Green |
| 1.5 mM~2.5 mM | Semipoisoning region | Yellow |
| 2.5 mM~3.5 mM | Poisioning region | Orange |
| 3.5 mM or higher | Dangerous region | Red |

| Control serum speciment (sample) | | | Coloration | Number of right answer | Correct answer rate |
|---|---|---|---|---|---|
| Autonorm | 1 mM | Control region | Green | 25 | 100% |
| Pathonorm | 1.6 mM | Semipoisoning region | Yellow | 24 | 96% |
| Precinorm | 2.5 mM | Poisioning region | Orange | 24 | 96% |
| Model serum | 3.5 mM | Dangerous region | Red | 25 | 100% |

Fig. 10]

Schematic diagram of a measuring apparatus
according to the present invention

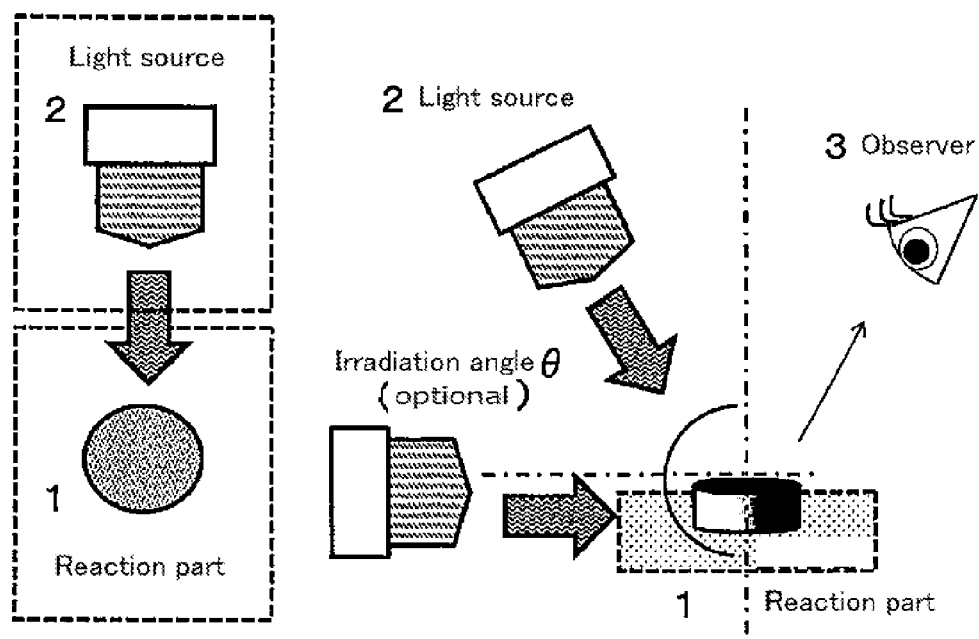

Influence of illuminance to the reaction completion time

Electronic absorption spectrum of photochemial tautomer originated from F28 tetra-phenyl porphyrin in the reagent composition in Example of this invention Electronic absorption spectrum in the reagent composition after the F28 tetra-phenyl porphyrin complex was irradiated in Example of this invention

LITHIUM MEASUREMENT METHOD

CROSS REFERENCE TO RELATED APPLICATIONS

This application is a National Stage of International Application No. PCT/JP2012/081742 filed Dec. 7, 2012, claiming priority based on Japanese Patent Application No. 2012-245766, filed Nov. 7, 2012, the contents of all of which are incorporated herein by reference in their entirety.

TECHNICAL FIELD

The present invention relates to a method for measuring lithium in a specimen of biomaterial such as urine, serum, plasma and blood test samples and in an aqueous solution such as environment samples including drinking water.

BACKGROUND ARTS

It is known that lithium-containing mood stabilizers are effective in medical treatment of manic-depressive illness, epilepsy and bipolar disorder, so that they are used widely. However, it is necessary to control or limit the concentration of lithium in a patient blood sample within a limited proper range when they are administrated to patients.

Generally, a lithium carbonate tablet (oral administration) is prescribed as mood stabilizer together with other therapeutic drug for bipolar disorder (manic-depressive insanity) or the antidepressant. The lithium carbonate ($Li_2CO_3$), however, has such a characteristic that its administration effect is exhibited only when the concentration of lithium in blood arrives at nearly a "lithium poisoning level". In other words, when the drug is administered, the therapeutic drug monitoring (TDM) is indispensable so as to monitor the lithium concentration in blood, since a therapeutic range is very near to the poison level.

In practice, it is necessary to control or limit the concentration of lithium in a patient blood sample within a limited range of from 0.6 to 1.2 mEq/L. In fact, when the lithium concentration in serum is lower than 0.6 mEq/L, no anti-depressive effect is expected. On the contrary, excess administration over 1.5 mEq/L of the lithium concentration in plasma will result in the lithium poisoning. Overdose result in a fatal cause of symptoms of poisoning including tremor, alalia, nystagmus, renal disturbance and convulsion. Therefore, when a sign of latently dangerous symptoms of lithium-poisoning is observed, the treatment with such lithium-containing drug must be stopped and the concentration in plasma must be re-measured so as to take a necessary measurement and to ease the lithium-poisoning.

Thus, the lithium salt is an effective medicine in the treatment of patients suffering depression, bipolar disorder, epilepsy or the like, but overdose result in serious troubles. Therefore, when a lithium-containing anti-depressive drug is administered, it is indispensable to monitor the concentration of lithium in serum and to assure that the concentration is always kept with a limited range of from 0.6 to 1.2 mEq/L.

Therefore, it was requested to determine the concentration of lithium in serum quantitatively and several liquid reagent compositions that permit colorimetric determination of lithium for the clinical laboratory test have been developed.

Patent Document 1 discloses a reagent composition used to measure the concentration of lithium in a biological sample by using cryptideinofa.

Patent Document 2 discloses an analytical reagent which reacts with lithium ion, comprising a macrocyclic compound having a pyrrole ring and eight bromine (Br) atoms combined at β position of the pyrrole ring.

Non-Patent Document 1 discloses that lithium ion can be detected by a compound in which all hydrogen bonded to carbons of tetraphenylporphyrin are replaced by fluorine.

PRIOR ART DOCUMENTS

Patent Documents 1: JP-A1-07-113807
Patent Documents 2: EP 1283986 (B1)
Patent Documents 3: Japanese Patent No. 5100903
Non-patent Document 1: Analytical Chemistry Vol. 51, No. 9, pp. 803-807 (2002); K. Koyanagi et al., "Synthesis of F28 tetraphenylporphyrin and its use for separation and detection"

THE SUMMARY OF INVENTION

Problem to be Solved by the Invention

Known lithium reagent compositions, however, have such demerits or problems that they are poisonous compositions, that drug substances are expensive or are not supplied stably, and that most drug substances do not dissolve in water or, even soluble, deactivated in water, so that coloring reaction is very slow.

Patent document 2 was developed to solve the above problems and permits use of color developing technique. The method of Patent Document 2, however, requires a dilution operation of a specimen since the sensibility is too high and the specification of the lithium reagent composition requires a range of over pH 11, so that it is easily deteriorated with $CO_2$ in air and hence measured data are not stable. Still more, no concentrated aqueous solution other than aqueous solutions of sodium hydroxide and of potassium hydroxide for a range of over pH11 is available in practice uses, so that it is difficult to keep a constant concentration. These concentrated aqueous solutions are hazardous substances which are difficult to be handled so that use of which should be avoided. Special containers are required for their storage and a larger scale special equipment or installation is required in their handling. Therefore, this technology is difficult to apply to on-site monitoring and POCT (Point Of Care Testing).

The reagent composition used for measuring of lithium quantitatively disclosed in Patent Document 1 is completely different from the present invention and can be used only at pH 12. As stated above, in a range of over pH 11, there is no practical concentrated aqueous solution other than those of sodium hydroxide and of potassium hydroxide which is hazardous substances which are difficult to be handled and a larger scale special equipment or installation is required for their supplement.

The document of Koyanagi et al., of the non-Patent Document 1 teaches that lithium ion can be separated and detected by using F28 tetraphenylporphyrin. However, extraction with oily poisonous chloroform is necessary to perform the separation and detection of lithium ion. In fact, direct determination of lithium in aqueous solution without complicated pretreatment was impossible. Thus, there was a problem that rapid and quantitative measurement of lithium ion in serum was impossible. In fact, detection of lithium ion in aqueous solutions by using F28 tetraphenylporphyrin is not easy, so that quantitative measurement of lithium ion with this compound have not been realized until now.

The conventional lithium reagents require a large-sized measuring instrument having a power supply such as a biological-chemistry automatic-analysis machine. In order to overcome such requirement, the present inventors developed a technical disclosed in Patent Document 3. In the Patent Documents 3, the claimed lithium reagent composition permits to measure the lithium concentration (quantitatively) in aqueous solutions such as biomaterial specimen and environment samples by a small instrument such as a colorimeter or by visual detection at an ordinary temperature and under a normal pressure.

This measuring method of Patent Document 3 is based on detection of difference in the concentration level by the concentration degree in same color tone. For example, a concentration difference in red-color and vermilion color for example is compared. Therefore, there is such a problem that lithium detection in a wider or meaningful range can't be carried out clearly, so that it is difficult to use the measuring method of Patent Document 3 for patients whom lithium intoxication is suspected such as emergency conveyance patients in emergency inspections. In fact, the measuring method of Patent Document 3 is difficult to apply or use in quick investigation without instrument.

The present invention was made in view of the problem mentioned above and provides a method which can measure and inspect the lithium concentration from an aqueous solution of biomaterial specimens such as urine, serum, plasma and blood and of environment samples, by visual observation or by using a simple colorimeter and by using the lithium reagent composition as a color-reaction reagent. In particular, the present invention provides a method for detecting, measuring and inspecting lithium clearly, simply and quickly at the emergency inspection in medical sites.

Means for Solving the Problems

In order to solve the problems, an embodiment of the present invention is a method for measuring lithium, characterized by contacting a specimen with an aqueous solution of a lithium reagent composition comprising a compound represented by following structural formula in which all hydrogens bonded to carbons of a tetra phenyl porphyrin are replaced by fluorine:

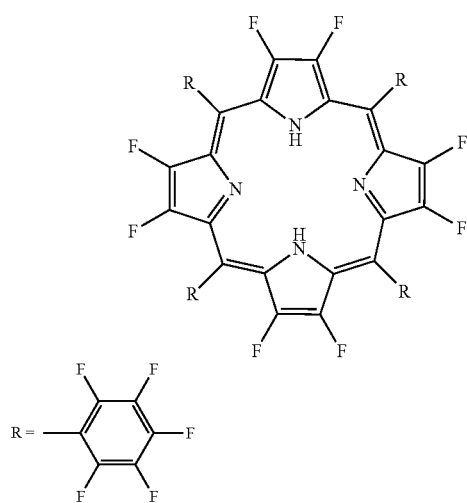

a PH regulator and a pH buffer, by irradiating the resulting solution with white light, and by detecting change in color tone by a visual observation or by detecting the sensitivity by a colorimeter.

A second embodiment of the present invention is a method, characterized in that the change in color tone is a change from a green color which is shown when a lithium coloration complex does not exist to the final red color through a yellow color and an orange color which are shown according to an increment of an amount of the lithium coloration complex.

A third embodiment of the present invention is a method, characterized in that the change in color tone occur in a range of 0.0 mM to 4.5 mM.

A fourth embodiment of the present invention is a method, characterized in that the specimen is biomaterial specimen including serum and plasma test sample.

A fifth embodiment of the present invention is a lithium measuring method, characterized in that the specimen is an environment sample.

In the lithium measuring method according to the present invention, the lithium reagent composition is used in a form of an aqueous solution including the compound represented by the above-mentioned structural formula in which all hydrogens bonded to carbons of a tetra phenyl porphyrin are replaced by fluorine used as a chelate agent, an organic solvent miscible in water, and a pH regulator. This aqueous solution is contacted with a specimen or a test substance such as of blood origin biological specimen including serum and plasma, urine and cell extract or environment sample to produce a chelate coloration complex with lithium ions in the test substance, so that a change in color is developed from a yellow color to a red color. Developed color depends on the lithium concentration. According to the principle of this invention, the resulting solution is then is irradiated with a predetermined quantity of white light to produce photochemistry enantiotropy variant of unreacted chelate ligand, so that coloration of a green color dependent to the lithium concentration is produced. As a result, a clear color change can be observed in a range of the lithium concentration from 0.0 mM to 4.5 mM in the test substance and this clear or sharp change in color tone can be detected easily by visual observation or by a simple colorimeter. In the lithium measuring method according to the present invention, the test substance is an aqueous solution such as serum and plasma test sample.

Advantages of Invention

In the lithium measuring method according to the present invention, the a specimen or test substance is contacted with an aqueous solution of the lithium reagent composition including the compound represented by the above-mentioned structural formula in which all hydrogens bonded to carbons of a tetraphenyl porphyrin are replaced by fluorine, a PH regulator and a pH-value buffer, and then the resulting solution is irradiated with or exposed to white light (or monochromatic light if reactable). It was found that a sharp vivid color change from green color to red color through yellow color of the resulting solution can be observed in a range of 0.0 mM to 4.5 mM of the lithium concentration in the specimen. The change in color is dependent to the lithium concentration. Thus, the lithium concentration contained in the aqueous solution added to the specimen can be determined by visual observation or by a simple colorimeter.

In fact, the lithium concentration in a serum test substance or a living-body specimen can be detected or judged quickly by naked eyes, because the color development is vivid and sharp as mentioned above and because an quantity of lithium in the serum test substance or a living-body specimen can be determined quickly by using a popular type small spectrophotometer. The resulting informational can be used also as a control index in the TDM therapeutic for instance. The lithium measuring method according to the present invention is applicable to a quantitative analysis of a large number of test substances in a clinical chemical automated analyzer in a short time.

The measuring method according to the present invention permits to detect or to measure the lithium concentration by visual observation or by using a simple portable colorimeter, through a change in color tone, by using the lithium reagent composition as a color-reaction reagent and by contacting it with an aqueous solution of living-matter specimen such as urine, serum, plasma and blood or of an environment sample, in opposition to the conventional techniques for measuring the lithium concentration in which a large-sized special-purpose machine was needed.

In particular, by using the present invention, the lithium concentration in case of the emergency inspection in a medical site can be judge quickly immediately after a serum as a specimen is taken

BRIEF EXPLANATION OF DRAWINGS

FIG. 7 [Table 2] showing an influence on measured values caused by hemolytic hemoglobin by sub-wavelength correction according to the present invention FIG. 8 [Table 3] showing evaluation of lithium concentration by visual observation in the prior art.

FIG. 9 [Table 4] showing evaluation of lithium concentration by visual observation according to the present invention.

FIG. 10 An illustrative drawing of a units for irradiating a test substance with white light according to the present invention.

MODE FOR CARRYING OUT THE INVENTION

Figures 1, 2:
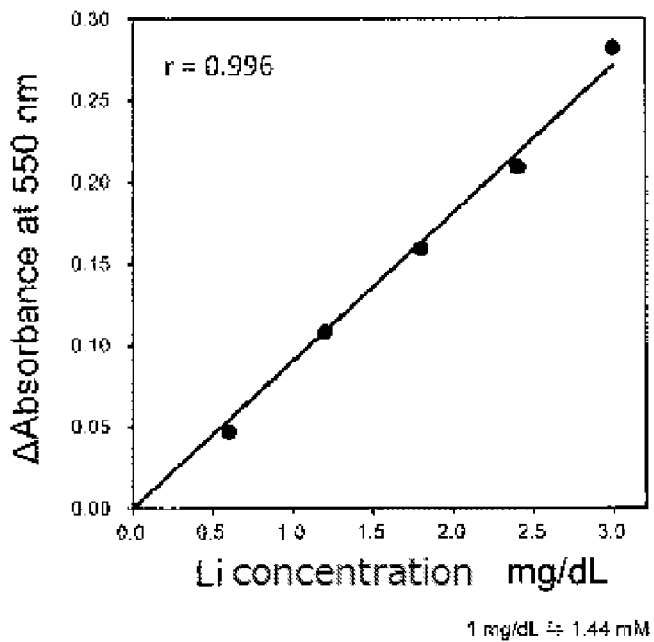
FIG. 1 A table for calculating the optimum concentration of F28 tetraphenylporphyrin according to this invention FIG. 2 A graph of ultraviolet-visible light spectrophotometer obtained in the result of Example 1 according to this invention.

Inventors studied lithium reagent compositions which can be used for measuring a concentration of lithium in serum and blood plasma quantitatively and more simply and focused on a compound represented by the following general formula:

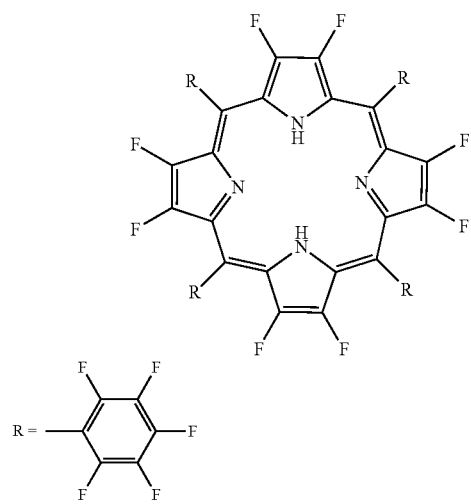

in which all of hydrogen atoms bonded to carbons of a tetraphenylporphyrin ring are replaced by fluorine atoms (the above compound is called herein "F28 tetraphenylporphyrin") having the total number of fluorine of 28, among the macro cyclic compound disclosed in non-Patent Document 1, and found the lithium reagent composition used in the measuring method according to the present invention.

Patent Document 2 discloses similar lithium reagent compositions comprising a macro cyclic compound having pyrrole rings in which eight bromine atoms (Br) are boned to β position of the pyrrole ring, to provide an analytical reagent which can react with lithium ions. This compound, however, is difficult to react with lithium if pH is not in an alkali side above pH 11. In case of the F28 tetraphenylporphyrin disclosed the Patent Document 3, the reaction occurs in a range of pH 5 to pH 12, so that the F28 tetraphenylporphyrin is used as a chelating reagent in the present invention to determine the quantity of lithium ions in an aqueous system.

The present invention permits to judge visually and clearly. We will explain firstly this lithium reagent composition used in the quantitative measurement.

In the present invention, the above-mentioned lithium reagent composition, especially the above-mentioned compound in which all of hydrogen atoms bonded to carbons of a tetraphenylporphyrin ring are replaced by fluorine atoms, which functions as a chelate agent (coloring agent) produces a lithium chelate color-development complex with lithium ions in an aqueous solution such as a biomaterial specimen and in an environment sample, so that only unreacted chelate ligand is changed to a structural isomer as a photochemical tautomer when it is irradiated with or expose to white light having a predetermined luminance. The resulting solution shows a green color when the lithium concentration in the specimen is lower than 0.5 mEq/L (=mol/L), a yellow color when the lithium concentration is above 0.5 mEq/L to 1.5 mEq/L, and a red color when the lithium concentration is higher than 1.5 mEq/L to 1.5 mEq/L. This coloration change conveniently correspond to the threshold value levels of the control region and of the poisoning region, so that the lithium concentration can be evaluated or detect clearly by visual observation and/or by colorimetry.

Inventors found also that the optimal concentration of the F28 tetraphenyl porphyrin in the lithium reagent composition is 0.1 to 1.0 g/L, preferably 0.5 g/L for the test samples used in the present invention in order to distinguish the lithium concentrations corresponding to the control region and to the poisoning region.

In connection with the pH regulator used in the present invention, the F28 tetraphenyl porphyrin compound which is a coloring agent (chelate agent) of the present invention does not couple with lithium ions at acid side of pH-value of lower than 5.0, and hence no color change take place. so that the quantitative detection of lithium is difficult.

In a range between pH 5 and pH 7, a specific reaction occurs between the color developer and lithium ion but the coloring reaction speed is slow. In a range between pH 8 and pH 11, the color developer reacts with lithium ion rapidly and a stable coloring complex can be formed. In alkaline side of higher than pH 11, a color tone of the chelating reagent and of coloring complex formed becomes instable in time. This may be caused by absorption of carbon dioxide in air, so that pH fluctuates. Therefore, it is necessary to use a pH modifier or pH buffer that can keep pH of the lithium reagent composition according to the present invention in a range from pH 7 to pH 12, preferably from pH 8 to pH 11.

The pH modifier can be selected from alkali medicine including sodium hydroxide, potassium hydroxide and ammonia, acid medicine including acetic acid, phosphoric acid, citric acid, carbonic acid, bicarbonic acid, oxalic acid, hydrochloric acid, nitric acid and their salts. The pH modifier may be pH buffer and may be selected from citric acid, carbonic acid, bicarbonic acid, phosphoric acid, succinic acid, phthalic acid, ammonium chloride, sodium hydroxide, potassium hydroxide, MES as Good's buffer, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, CAPS and their salts.

The lithium reagent composition according to the present invention presents the specific color reaction for lithium in a range of from pH 5 to pH 12 by incorporating the pH modifier.

It is indispensable that the solvent (polar solvent) used in this invention is an organic solvent that is compatible with water. The solvent can be a solution consisting mainly of organic solvent or an aqueous solution in which an organic solvent is added, provided that the solvent can be mixed uniformly with an aqueous solution such as serum, blood plasma and eluate which is a test sample. In fact, since a test sample to be measured is in a form of an aqueous solution when the concentration of lithium in sample is determined by a general-purpose type automated analyzer and by an ultraviolet-visible light spectrophotometer, it is desirable that the reagent composition is in a form of an aqueous solution.

The organic solvent is preferably chosen from dimethyl sulfoxide (DMSO), dimethyl formamide (DMF) and dimethyl acetamide (DMA).

In actual products, a suitable stabilizer is incorporated in the reagent composition according to this invention. In an embodiment, a surfactant is used as the stabilizer. The surfactant improves the dispersibility of F28 tetraphenylporphyrin compound and prevents suspensions originated from the sample during the coloring reaction. Therefore, the stabilizer is used to assure such effect.

The stabilizer may be nonionic surfactant or anionic surfactant. The nonionic surfactant may be sorbitan fatty acid ester, pentaerythritol fatty acid part ester, propylene glycol monofatty acid ester, glycerin fatty acid monoester, polyoxyethylene alkyl ether, polyoxyethylene alkyl phenyl ether, polyoxyethylene polyoxypropylene glycol, polyoxyethylene fatty acid part ester, polyoxyethylene sorbitol fatty acid part ester, polyoxyethylene fatty acid ester, fatty acid di-ethanol amide, fatty acid ethanol amide, polyoxyethylene fatty acid amide, polyoxyethylene octylphenyl ether (Triton X-100®), p-nonyl phenoxy polyglycidol or their salts. Preferable nonionic surfactants are polyoxyethylene octylphenyl ether (Triton X-100®) and p-nonyl phenoxy polyglycidol.

The anionic surfactant as stabilizer may be alkyl sulfate ester salt, polyoxyethylene alkyl ether sulfate salt, polyoxyethylene phenyl ether sulfate salt, alkyl benzene sulfonate and alkane sulfonate. Typical anionic surfactant is selected from sodium dodecyl sulfate, sodium dodecyl benzene sulfonate and sodium polyoxyethylene alkylphenyl ether sulfate.

The lithium reagent composition according to the this invention can contain more than one masking reagent, in order to avoid disturbance caused by other ions than lithium, which may present in the sample, to suppress oxidation of the reagent composition and to improve the storage stability. The masking reagent may be not necessary if there are few ions other than lithium.

The masking reagent which can be added to the lithium reagent composition according to the present invention may be selected from triethanol amine, ethylenediamine, N,N,N',N'-tetrakis(2-pyridylmethylethylenediamine (TPEN), pyridine, 2,2-bipyridine, propylene diamine, dimethylene triamine, dimethylene triamine-N,N,N',N'',N''-penta acetic acid (DTPA), trimethylene tetramine, trimethylene tetramine-N,N,N',N'',N''',N''''-hexaacetic acid (TTHA), 1,10-phenanthroline, ethylene diamine tetraacetic acid (EDTA), O,O'-bis(2-aminophenyl)ethyleneglycol-N,N',N'-tetraacetic acid (BAPTA), N,N-bis(2-hydroxyethyl)glycine (Bicine), trans-1,2-diaminocyclohexane-N,N,N',N'-tetraacetic acid (CyDTA), O,O'-bis(2-aminoethyl)ethyleneglycol-N,N,N',N'-tetraacetic acid (EGTA), N-(2-hydroxyl) imino diacetic acid (HIDA), imino diacetic acid (IDA), nitrile triacetic acid (NTA), nitrile trimethylphosphonate (NTPO) and their salts. Triethanol amine is preferably used.

The lithium reagent composition according to this invention may include antiseptics to prevent degradation caused by microorganism. The antiseptics are not limited especially and may be sodium azide and Procline®. An amount of antiseptics is not especially limited and may be a concentration used generally as an antiseptic. For example, in case of sodium azide, the amount of antiseptics is about 0.1% by mass to a reaction solution. The antiseptics are usually prescribed for products which are stored for longer term duration.

To guarantee a long-term storage, the lithium reagent composition according to the present invention can be stored separately in a form of a kit for measuring lithium reagent comprising two separate reagents which are mixed just before measurement to realize the lithium reagent composition. In fact, a first reagent comprises the pH modifier and the stabilizer, while a second reagent comprises the compound represented by the following general formula:

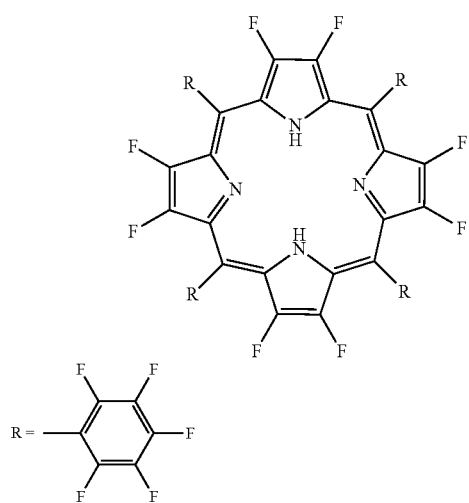

in which all of hydrogen atoms bonded to carbons of a tetraphenylporphyrin ring are replaced by fluorine atoms, the water-miscible organic solvent, pH modifier or pH buffer and the masking reagent.

The lithium reagent composition used in the lithium measuring method according to the present invention is an aqueous solution containing the compound represented by the above-mentioned structural formula in which all hydrogens bonded to carbons of a tetra phenyl porphyrin are replaced by fluorine, as chelate agent, an organic solvent miscible in water and a pH regulator. When the aqueous solution is contacted with lithium ions in a serum and a plasma test sample, a change in color tone caused by a lithium complex produced is observed. If the aqueous solution is irradiated with a light having a predetermined intensity, a vivid green color caused by the F28 tetra-phenyl porphyrin which was not reacted with lithium ions can be observed. On the other hand, a red color developed with the color-development complex between F28 porphyrin and lithium ions is remained without change. As a result, a clear vivid color change from green color to red color through yellow color can be observed in a lithium concentration range of 0.0 mM to 4.5 mM. This invention was made by this founding and is based on a principle of the clear vivid color change. In the lithium measuring method according to the present invention, the change in clear vivid color tone in a specimen of an aqueous solution containing a serum and plasma test sample can be observed or detected easily by naked eyes or by a colorimeter.

Alternatively or additionally, the absorbance and spectrum of lithium complex may be measured by using the lithium reagent composition without or with the lithium measuring method by visual observation. Or, a quantitative value in an unknown specimen can be calculated from known lithium concentrations in the standard samples. In particular, in the absorbance and the spectrum of lithium complex, the sensitivity is measured at a measurement wave length of 560-nm or in its near wave-length range of from 530 nm to 550 nm. Or, the sensitivity is measured at a measurement wave length of 570 nm or in a vicinal wave-length range of from 565 nm to 650 nm to determine the lithium concentration.

In the measuring method disclosed in the above-mentioned prior art, a test sample of serum and plasma is contacted with the lithium reagent composition and the resulting color development of the lithium complex or absorbent or spectrum is measured. The resulting sensitivity is measured preferably at a wave-length of 560 nm or near wave length range of from 530 nm to 550 nm in the spectrum, or the resulting sensitivity is measured at a wave-length of 570 nm or in a vicinal wave length range of from 565 nm to 650 nm to determine a quantitative value of lithium.

At the wavelength of 550 nm or in the vicinity range of from 530 nm to 560 nm, the calibration curve has better linearity than that of in case of the Soret band (wavelength range from 400 nm to 500 nm in which the maximum absorbent is obtained), so that the concentration can be calculated easily by a small size colorimeter or a spectrophotometer. Still more, since change in color tone from yellow to red is very sharp, the level of concentration can be judged by visual observation or naked eyes. In the conventional technique, a large-sized special-purpose machine was needed to measure the lithium concentration. In the present invention, the concentration of lithium can be measured by a small portable colorimeter or the UV-visible spectrophotometer which is currently used widely, so that the present invention can be realized in a form of a POCT (Point Of Care Testing) kit.

Now, Example 1 of the lithium reagent composition used in the present invention is described.

EXAMPLE 1

(Lithium Reagent Composition Sample 1)

In this Example 1, a first reagent as a pH buffer solution and a second reagent as a coloring reagent solution were prepared firstly. Then, two reagents of the first and second reagents were mixed just before measuring operation to prepare a lithium reagent composition according to the present invention. Although these two reagents can be stored in a form of mixer but it is advisable to store them separately and mix together just before measuring operation to avoid deterioration of the reagents during a long storage time duration.

Now, we will explain how to prepare the reagent composition according to the present invention in details.

To begin with, the first reagent (pH buffer solution) is prepared. Followings are the composition of the first reagent.

(1) First reagent (as stabilizer and buffer solution):
  chelating reagent: none
  organic solvent; none
  stabilizer (dispersant: nonionic surfactant): 1.0% by weight of TritonX-100® (polyoxyethylene octylphenyl ether)
  masking reagent: 10 mM of triethanol amine Into a mixture of above components, 7% by weight of ammonium chloride was added to adjust to pH 10. Then, the total volume was increased to 1 liter with purified water and stored in a usual storing container. If a proportion of TritonX-100® (polyoxyethylene octylphenyl ether) is lower than 1.0% by weight, turbidity may occur in some cases. On the contrary, if excess stabilizer is used, foam will be generated in a reactor vessel. Such turbidity or forming may influence the reproducibility of measurement, so that a range of range of 0.1 to 5.0% by weight is preferable and 1.0% by weight is more preferable.

In this Example, the masking reagent is 10 mM of triethanol amine. If an amount of the masking reagent is short, a satisfactory masking effect will not be obtained in such samples that contain excess foreign ions other than lithium. On the contrary, excess masking reagent will mask lithium ion itself, resulting in a cause of errors in measurement. Therefore, a range of 1.0 to 100 mM is preferable and 10 mM is more preferable.

The second reagent (color developing reagent solution) is produced as follows.

(2) Second reagent (as color developing reagent solution):
chelating reagent: 0.5 g/L of F28 tetraphenylporphyrin
organic solvent; 20% by weight of dimethyl sulfoxide (DMSO)
stabilizer (dispersant: nonionic surfactant): 1.0% by weight of TritonX-100® (polyoxyethylene octylphenyl ether)
masking reagent: 10 mM of triethanolamine Into a mixture of above components, 0.05M (mol/L) of MOPS (Good's buffer) was added to adjust to pH 7.0. Then, the total volume was increased to 1 liter with purified water and the resulting solution was stored in a usual storing container.

In the quantitative measurement of lithium in serum of laboratory test, the precision of lithium concentration is requested in a wider range from 0.6 mM to 3 mM. In Example 1, we found that precise measurement can be performed when the concentration of F28 tetraphenylporphyrin compound is set in a range of 0.1 to 1.0 g/L, preferably 0.5 g/L, for the above-mentioned lithium concentration. In fact, in the concentration range of lithium of 0.6 mM to 3 mM, measurement of lithium can be performed in the range of 0.1 to 1.0 g/L, preferably 0.5 g/L in the final reagent composition. If the concentration is lower than the above limit, a reaction between F28 tetraphenylporphyrin and lithium ion is not sufficiently proceed. On the contrary, if the concentration exceeds the above limit, another trouble of increase in the absorbance of a blank of F28 tetraphenylporphyrin compound will occur. Therefore, the concentration of 0.5 g/L is preferably used.

In more details, the reaction between F28 tetraphenylporphyrin and lithium ion is a reaction of equal mole ratio of 1:1 to form a chelate complex. When a test sample containing 3 mM of lithium is reacted with the reagent composition according to the present invention under the condition of Example 1, the concentration of lithium in the reaction system becomes 0.02 mM. Therefore, the concentration of F28 tetraphenylporphyrin compound must exist at a concentration of higher than 0.02 mM to effect the reaction sufficiently (neither too much nor too little).

In the complex-forming reaction (coloring reaction) between a chelating reagent and metal ions, it is necessary in general to use the chelating reagent (F28 tetraphenylporphyrin) at an amount of from equal mol to ten times mols with respect to a reactant or a subject to be tested (lithium). As is shown in FIG. 1 which shows the optimum concentrations of F28 tetraphenylporphyrin, the reagent composition is prepared in such a manner that the concentration of F28 tetraphenylporphyrin during the reaction time becomes from equal mol to 10 times. In practice, it is preferable to use a concentration of the chelating reagent in the reagent composition of 0.5 g/L (5 times) rather than 0.1 g/L (same size) so as to permit to use in wider measuring conditions, because parameters of dosages at measuring reaction of an added amount of the reagent composition and of an amount of sample to be tested depend on measuring apparatus and desired thresholds and vary. For example, in case of a measuring apparatus whose measuring accuracy is not so high, an amount of sample may be increased to two times to five times to that of Example 1. To prepare to such cases, it is advisable to use the concentration of 0.5 g/L (5 times) of the reagent composition which is enough amount of reagent for the reaction. Excess amount of higher than 10 times has no advantage because increased amount of the reagent may not significant advantage in the kinetic of coloring reaction but rather increase a trouble of elevation of blank level.

What is necessary is to satisfy the reaction condition in the mole ratio between chelating reagent and lithium. For example, when the concentration of chelating reagent (F28 tetraphenylporphyrin) in the second reagent is 1.0 g/L, an amount of the second reagent which is added to the reaction can be reduced to a half. Or, when an amount of sample is reduced to a half, an amount of the chelating reagent can be reduced to a half.

In Example 1, the concentration of F28 tetraphenylporphyrin is 0.5 g/L. The optimum concentration of F28 tetraphenylporphyrin is 0.1 to 1.0 g/L that satisfies the reaction condition in mole and lowers to the minimum blank level.

An amount of dimethyl sulfoxide (DMSO) is 5 to 30% by weight. When this amount is shorter, dispersion of F28 tetraphenylporphyrin in a solution become poor. On the contrary, if excess amount of dimethyl sulfoxide result in increase of the organic solvent in the reagent composition. Therefore, a preferable amount is 20% by weight. When it is desired to reduce the amount of organic solvent, an amount of less than 10% by weight can be used without any problem.

F28 tetraphenylporphyrin used in this Example 1 has a structure represented by the following formula:

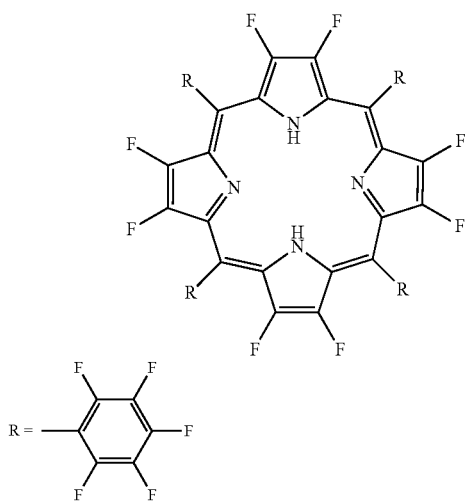

in which all hydrogens bonded to carbons of a tetraphenylporphyrin are replaced by fluorine atoms.

(3) Now, we will explain how to prepare a calibration curve of the lithium reagent composition prepared by mixing the first reagent with the second reagent for samples whose lithium concentrations are known.

In Example 1, 720 µL of the first reagent (buffer solution) and 240 µL of the second reagent (coloring reagent solution) were added to 6 µL of a sample. In this case, the first reagent has a buffer capacity at pH10. After the first and second reagents and the sample are mixed, the resulting mixture of a test liquid has about pH 10.

Thus, when F28 tetraphenylporphyrin according to the present invention is used as a chelating reagent, a color developing reaction can be carried out in a pH range of from pH 5 to pH 10. In fact, the present invention provides a reagent for lithium measurement possessing a strong pH buffering action in a range of lower than pH 10, so that fluctuation of pH caused by absorption of $CO_2$ in air can be reduced. And hence, an adverse effect to measured values can be avoided, and it is possible to store the measuring reagents in general-purpose containers.

It is possible to mix the first reagent with the second reagent just before usage and to add the resulting mixture to the same volume of sample. In this case, 940 μL of the liquid mixture can be added to 6 μL of a sample.

Figure 4:
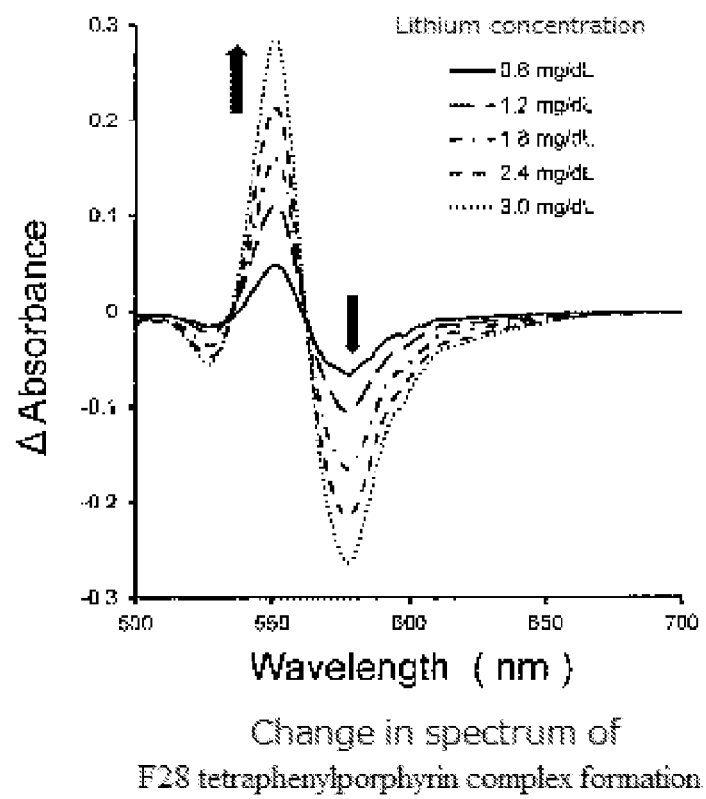
FIG. 4 A graph showing changes in spectrum (color reaction) when F28 tetraphenylporphyrin-lithium complex is formed in Example 1 according to this invention.

A test sample was added to the resulting mixture of pH 10 to effect a reaction at ambient temperature for 10 minutes and then an absorbance at 550 nm was measured by a ultraviolet-visible light spectrophotometer (HITACHI, U-3900 type), the blank being the test sample. FIG. 2 shows the result which is a relation between absorbance and Li concentration (mg/L). FIG. 4 is a graph showing change in spectrum in a visible light range when F28 tetraphenylporphyrin-lithium complex is formed.

For metal complex of tetraphenylporphyrin, the maximum sensitivity is obtained at a wavelength range of so-called Soret band (about from 380 nm to 460 nm). However, in the present invention, this Soret band range is not used but a wavelength of 550 nm or in the vicinity range of from 530 nm to 560 nm is used, so that complicated dilution operation and dilution means or an auxiliary facility are not necessary in the present invention.

Figure 3:
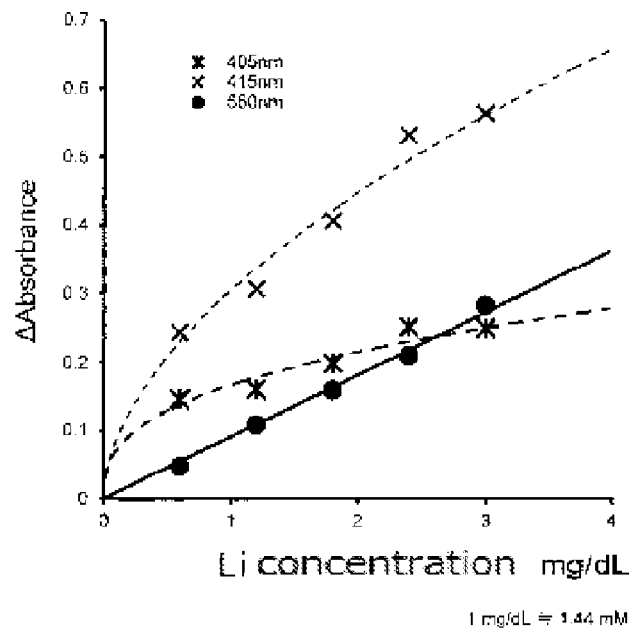
FIG. 3 A graph of the calibration curve at different wavelengths in Example 1 according to this invention.

As is shown in FIG. 3 which is a graph showing a relation between Li concentration (mg/dL) and absorbance (wavelength of 380 nm (*), 415 nm (x), 550 nm (●)), a better linearity in the calibration curve can be obtained when a wavelength of 550 nm or in the vicinity range of from 530 nm to 560 nm is used than other cases when wavelengths of so-called Soret band are used. Therefore, the precise concentration can be calculated easily by a simple colorimeter or spectrophotometer. Still more, change in color from yellow to red is very sharp, so that a level of the concentration can be detected easily by naked eyes. In the conventional technique, an apparatus of a large scale for exclusive use is necessary to measure the lithium concentration, while, in the present invention, the lithium concentration can be measured easily by a portable colorimeter or ultraviolet-visual light spectrophotometer which is used widely. The present invention can be constructed in a form of a POCT kit.

In the graph of FIG. 3, the same reagents of the 1st reagent and 2nd reagent used in Example 1 effected at a wave length of 550 nm (●) were added also for the Soret band range of 405 nm (*) and 415 nm (x). In case of the wave length of 405 nm and 415 nm, however, the specimen was diluted at 5 times because the sensitivity became too high. FIG. 3 reveals such a fact that a linear calibration curve can be obtained in case of 550 nm of the present invention, while the calibration curves for wave length of 405 nm and 415 nm do not have linear curves.

FIG. 4 shows changes in spectrum when F28 tetraphenylporphyrin-lithium complex is formed. It is confirmed clearly from FIG. 4 that the absorbance will increase linearly with the increase of lithium concentration from 6 mg/dL to 1.2 mg/dL, 1.8 mg/dL, 2.4 mg/dL and 3.0 mg/dL. An absorption peak of 415 nm (Soret band) which is typical for porphyrin-metal complex and an absorption peak of 550 nm (shown in FIG. 4) increase and an absorption peak of 570 nm (also shown in FIG. 4) decreases in proportion to the concentration of lithium. Therefore, a difference in absorbance can be calculated in these absorption peaks. In the present invention, the wavelength of 550 nm is preferably used as a photometry measuring wavelength because of good linearity in the calibration curve.

It is possible to select a wavelength range from 540 nm to 560 nm as the photometry measuring range in place of the wavelength of 550 nm used in Example 1. In fact, some measuring equipment may not have a photometry filter for 550 nm. In such case, the photometry measuring wavelength can be selected from a wavelength range in the vicinity such as 540 nm or 560 nm where the sensitivity is also high. A wavelength of 570 nm also can be used as a photometry measuring wavelength, since decrease in the sensitivity of absorbance at 570 nm is also quantitative as is shown in FIG. 4. Therefore, a difference in absorbance (Δ Abs) at 570 nm also can be calculated with a reference of the reagent as a blank.

In such a rare case that some contaminants that interfere at the wavelength of 550 nm are produced in a sample of patient and erroneous data are produced at the wavelength of 550 nm, it is possible to select a wavelength of 570 nm or in the vicinity of from 565 nm to 650 nm as photometry measuring wavelength to avoid such trouble and to calculate the lithium concentration from a decrease in the sensitivity as a difference in absorbance.

Now, we will explain a method for correcting a measurement error in the lithium measuring method of this invention.

It is known that two absorption peaks (beta band and alpha band respectively) caused by hemoglobin which is a disturbance factor are observed at about 540 nm and about from 560 nm to 650 nm for such a test substance as hemolyzed serum. We found such that a positive error occur with respect to an actual measured value when a test substance which contains a high concentration of hemoglobin is contacted with the reagent composition according to the present invention, because the absorption at 540 nm originating from beta and alpha bands of hemoglobin overlaps with the absorption at 550 nm which is a wave length according to the present invention.

Namely, the positive error caused by hemoglobin occurs in a measured sensitivity at 550 nm which is the total of (a sensitivity of lithium-F28 tetra-phenyl porphyrin-complex at 550 nm)+(a sensitivity of haemoglobin at 550 nm).

We noticed such a fact that a ratio of two sensitivities of haemoglobin at 550 nm and at 600 nm is almost same. In other words, the sensitivity of haemoglobin at 550 nm is equal to a sensitivity of haemoglobin at 600 nm, so that the sensitivity of haemoglobin at 550 nm can be cancelled by the sensitivity of haemoglobin at 600 nm. Therefore, a correct sensitivity at 550 nm can be obtained by an equation of the sensitivity: The sensitivity at 550-nm=a sensitivity of lithium-F28 tetra-phenyl porphyrin complex at 550 nm+a sensitivity of haemoglobin at 550 nm−a sensitivity of haemoglobin at 600 nm.

Now, we will explain how to measure the lithium concentration correctly with the lithium reagent composition of according to the present invention from experimental data of Example 1.

Results of Experiment in Ultraviolet-Visible Light Spectrophotometer (HITACHI, U-3900 Model)

FIG. 2 shows an experiment result measured by an ultraviolet-visible light spectrophotometer (HITACHI, U-3900 model). An axis of abscissa is known lithium ion concentrations (Li concentration, mg/dL) and an axis of ordinate is difference in absorbance measured by the ultraviolet-visible light spectrophotometer at a wavelength of 550 nm.

FIG. 2 reveals that a good linearity of a calibration curve is obtained in a relation between the absorbance and the lithium concentration.

Figures 5, 6:
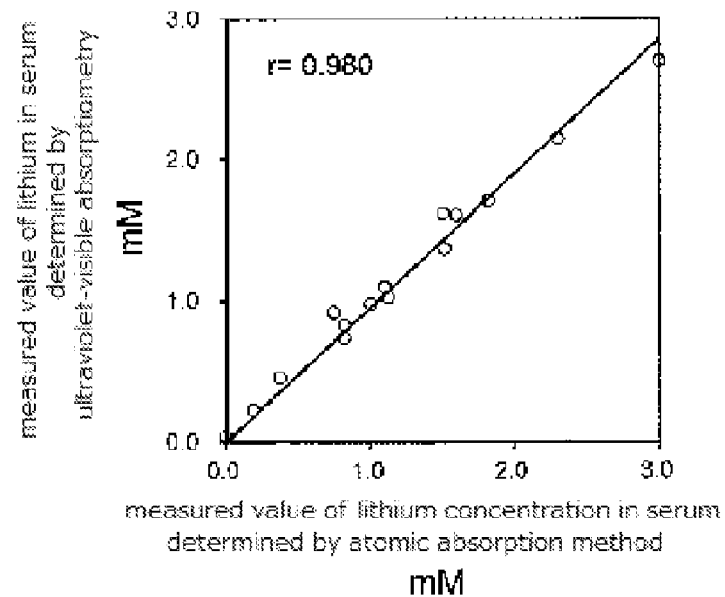
FIG. 5 A graph showing a correlation between measured values of serum samples in Example 1 according to this invention and measured values obtained by the atomic absorption method (conventional method).
FIG. 6 [Table 1] showing a comparison with measured values obtained by using an automated analyzer in which the control serum samples were used.

Correlation Test Between Atomic Absorption Method (Conventional Method) and the Method According to this Invention for a Serum Sample FIG. 5 is a graph showing a correlation of measured values between the measuring method of Example 1 according to this invention shown in FIG. 2 and the conventional atomic absorption method (conventional method) carried out for the same serum sample. Measured values obtained by the conventional atomic absorption method (conventional method) are plotted on axis of abscissa (X), while measured values according to this invention are plotted on axis of ordinate (Y). A regression line shown in FIG. 5 shows a good correlation of more than 95%. This result reveals that lithium in a serum sample can be determined quantitatively by an ultraviolet-visible light absorptiometry with the reagent composition according to the present invention.

Comparison of Measured Values Carried Out by Automatic Analysis for Control Serum Samples The lithium concentration was measured for following control serums samples:
Precinorm U (Roche)
Precipath U (Roche)
Pathonorm H (SERO AS)
Auto norm (SERO AS)
in which the lithium concentration is valued by using a biochemistry automated analyzer (HITACHI, H-7700 model) at a photometry measuring wavelength of 546 nm (which is a wavelength set in this analyzer and is near to 550 nm) by 1 point end method.

Device Parameters:
Reagent: 0.24 mL
Sample: 0.005 mL
Photometry wavelength (main/sub): 546 nm/700 nm
Measuring time: 10 minutes
Temperature: 37° C.
1 point end: increasing method Results shown in [Table 1] of FIG. 6 proves such a fact that that measured values obtained by the present invention coincide with the guaranteed values under the above conditions, so that it was confirmed that the lithium concentration in serums can be measured satisfactorily by an automated analyzer for clinical tests.

Results shown in [Table 1] of FIG. 6 proves such a fact that that measured values obtained by the present invention coincide with the guaranteed values under the above conditions, so that it was confirmed that the lithium concentration in serums can be measured satisfactorily by an automated analyzer for clinical tests.

In the above Example, the lithium reagent composition is a two components type in which a first reagent and a second reagent are mixed before use. On the other hand, in a lithium measuring method by a microplate reader and in a lithium detecting method by visual observation which will be explain later, one pack type lithium reagent composition is used and a 96 well plate is used as a specimen container. Therefore, experiments were carried out by using one pack type lithium reagent composition which will be explained in Example 2 (Lithium reagent composition sample 2) prepared on the base of composition of Example 1.

In order to confirm that the same method as Example 2 which will be explained later can be realized in Example 1, a lithium detection test by visual observation was carried out also for the lithium reagent composition of Example 1 by adjusting an amount of test sample. In this case, when the test sample was irradiated with white light, following color change was observed depending to the concentration of lithium in the test sample:
Green color: lower than 0.5 mEq/L (=mol/L)
Yellow color: from 0.5 mEq/L to 2.5 mEq/L
Red color: higher than 1.5 mEq/L This color change corresponds conveniently to the threshold value levels of the control region and of the intoxication region, so that lithium level can be detected clearly by visual observation or by colorimeter. The results of experiment using the lithium reagent composition of Example 1 was almost same as those obtained in Example 2 and hence details of experiment when the lithium reagent composition of Example 1 was used are not described here.

EXAMPLE 2

(Lithium Reagent Composition Sample 2)

A composition of Example 2 is substantially same as Example 1, but one pack type color-developing fluid is used in Example 2, while two pack type is used in Example 1, because of following reason:

When detection is carried out on a well plate of 96 wells for microplate readers, handling can be simplified to two operations for a sample and for color-developing fluid in case of one pack type. A complicated mixing operation can be carried out easily in case of Example 1 in which a cuvette container having a big capacity of 1 mL for a spectrophotometer is used, but such complicated operation for mixing the first reagent and the second reagent in a small well of the well plate is not easy in case of one pack type color-developing fluid. Therefore, one pack type color-developing fluid is used in Example 2 to facilitate the operation. In Example 2, above-mentioned surfactant and pH buffer are chosen so as not to give a bad influence to a material of the well which is polystyrene resin.

FIG. 7 shows the results of interference test in hemolysis effected by a microplate reader (CORONA SH1200) in [Table 2] when an error correction method is adopted to the method to determine the lithium concentration according to the present invention.

| (1) Coloring reagent (Lithium reagent composition 2): | | |
|---|---|---|
| Chelate agent: | F28 tetra-phenyl porphyrin | 0.17 g/L |
| Organic solvent: | Dimethyl sulfoxide (DMSO) | 5% by weight |
| Stabilizer (dispersing agent): | Sodium dodecyl sulphate | 1% t by weight |
|  | Triton X-100 | 1% by weight |
| Masking agent: | Triethanolamine | 10 g/L |
|  | Ethylenediamine tetraacetate dipotassium | 0.5 g/L |

Into a mixture of above components, pH regulator and a pH buffer were added to adjust to pH 10 and purified water was added up to the total volume of 1 liter. The resulting mixture was stored in a general-purpose preservation container.

(2) Hemolysis Specimen

A hemolysis specimen was prepared by adding a predetermined amount of Interference check A+® (Sysmex) as hemolysis haemoglobin into a basis serum containing 1.5 mM lithium. 240 muL of coloring reagent was added to 4 µL of the above-mentioned specimen and the resulting mixture was reacted t for 5 minutes.

Then, an absorbance of the specimen was measured by a microplate reader (CORONA SH-1200) to calculate the lithium concentration on the basis of the absorbance of standard substance at a main wavelength of 550 nm and at a subwavelength of 600 nm.

As explained above, in case of a hemolysis test substance, haemoglobin having an absorbance at 550 nm will be a positive disturbance for a measured value, if a photometry measurement is effected only with a wave length of 550 nm. Therefore, measurement was effected with two wave lengths of 550 nm and 600 nm so that two absorbance values are offset each other by calculating an absorbance at 550 nm-an absorbance at 600 nm. An influence of hemolysis can be canceled by this correction method. When an automated analyzer is used, it is sufficient to input, as parameters, 550 nm as main wavelength of and 600 nm as subwavelength.

FIG. 7 shows in [Table 2] that a difference from a correct value is only 2% in a corrected case (recovery=102%), while the difference increase to 25% if the correction method is not used (recovery=125%) at a concentration of haemoglobin of 1000 mg/dL. This result reveals that the above-mentioned correction measure according to the present invention is the very effective to determine the lithium concentration.

[Lithium Detection by Visual Observation]

Now, we will explain how to measure and detect the lithium concentration by visual observation according to the present invention.

FIG. 8 shows, in the [Table 3], a result of the correct answer rate obtained by a known technique described in Patent Document 3 which is another invention of this application. In this test, color development of test fluids was observed by naked eyes. In practice, the above-mentioned lithium reagent composition sample 2 was used as a coloring reagent. 240 muL of the coloring reagent was added to 4 µL of specimen and a reaction was effected for 5 minutes at ambient temperature. Then, developed color of specimens was observed by naked eyes of observers and a number of persons who gave a correct answer were counted. Each specimen having a predetermined concentration level was compared with standard samples each having a predetermined lithium concentration used as color tone references.

In this test, a color change from yellow color to red color was observed in the measured concentration ranges and color development of the control serum was consistent with the color tone references. Therefore, it is understood that the lithium concentration in a serum can be judged quickly and simply without using a special apparatus.

The correct answer rates for a yellow color of Auto norm 1 mM which is a control region and for a red color of model serum 3.5 mM which is a dangerous region are 100% for 25 judging persons, because of a clear color change from a yellow color to a red color. However, the correct answer rates became a little worse to 52% in cases for Pathonorm H 1.6 mM (semi-poisoning region) and Precinorm U 2.5 mM (poisoning region).

The present inventors studied to improve the above-mentioned method and arrived at the present invention.

In an embodiment of this invention, a test sample (a mixture of a specimen and the reagent composition) obtained in the above-mentioned prior art is irradiated with or expose to white light having a predetermined luminance, so that a portion of F28 tetra-phenyl porphyrin which did not reacted with lithium ions is changed to a structural isomer of photochemical tautomer, resulting in that following color is developed according to the lithium concentration in the specimen:

| 0.5 MEq/L (=Mol/L) or less | green color, |
| 0.5 MEq/L to 1.5 MEq/L | yellow color, |
| 1.5 mEq/L or more | red color. |

We found that this color change corresponds conveniently to threshold levels of a control region and a poisoning region, so that the color change is detectable clearly by visual observation or by a colorimeter.

FIG. 9 shows, in [Table 4], the result of judgment carried out for detecting the lithium concentration by visual observation according to the present invention. The results of 25 judging persons were such very good that the correct answer rate was 100% for a green color showing the control region of Auto norm 1 mM and for a red color showing the dangerous region of the model serum 3.5 mM, and 96% for the semi-poisoning region of Pathonorm H 1.6 mM and for the poisoning region of Precinorm U 2.5 mM.

In fact, optical tautomer is generated by the irradiation of white light only for a portion of F28 tetra-phenyl porphyrin which did not reacted with lithium to show a green color. When the lithium concentration is 4.3 mM, a percentage of unreacted chemical species (or optical tautomer generated) is not so high that a red color of sample is not changed and hence a red color is maintained. If the lithium concentration is within an intermediate region, a yellow color which is a neutral color between green and red is observed.

In usual detection by visual observation or by a colorimeter, a difference in density is detected to determine the concentration. In the present invention, however, a change in color tone (from green color to red color trough yellow color and orange color) itself is detected or observed. It is very rare case that such color tone change is detectable clearly at highly efficient.

Now, we will explain the detection method according to the present invention from the first step of sample preparation in details.

FIG. 10 illustrates an apparatus for changing only a portion of F28 tetra-phenyl porphyrin which did not reacted with lithium to the structural isomer as a photochemical tautomer by irradiating (or exposing) a specimen contained in a transparent container with white light having a predetermined luminance.

The lithium reagent composition sample 2 of Example 2 was prepared as the same reagent composition as Example 1. 1 mL of the lithium reagent composition sample 2 was added to a sample in transparent container or a cuvette for spectrometry in a reaction part (1) of FIG. 10. The cuvette is irradiated with white light of a LED light source (2).

Figure 11:
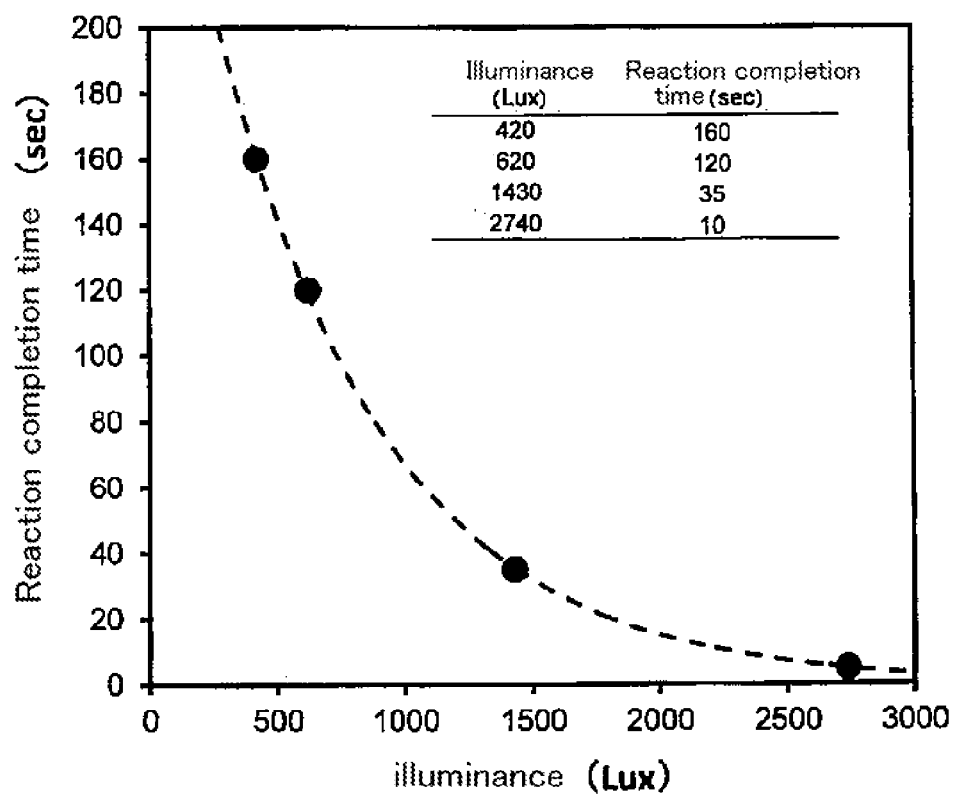
FIG. 11 A graph showing an influence of the irradiation on time duration required to complete the photochemical tautomerization reaction according to the present invention.

FIG. 11 is a measured graph showing a relation between time duration required to complete the photochemical tautomerization reaction (reaction completion time) and illuminance.

Intensity of the LED light source was measured by an illuminometer installed in the proximity of the spectrum cuvette. Termination (reaction completion time) of the photoisomerization reaction was determined by measuring an electron absorption spectrum and observing a shift of the spectrum from a wave-length band range of 400 nm to 600 nm (the spectrum before reaction) to a wave-length band range of 600 nm to 800 nm (the spectrum after photoisomerization).

FIG. 11 shows the results. It was confirmed that the photoisomerization reaction completes within 40 seconds with an illuminance of 1430 lux or more, while about 3 minutes is necessary to complete the reaction with an illuminance of 420 lux. The illuminance in a general office, a consultation room in hospital and an inspecting room is 750 lux from 300 lux. Therefore, the measuring method according to the present invention can be carried out quickly under a usual interior illumination in the usual institution without using a special light source.

In order to obtain an illuminance of higher than 1430 lux, it is sufficient to bring the LED light source near a specimen so as to complete the reaction more rapidly.

FIG. 11 is a graph showing an influence of the illuminance (lux) which is a quantitative index of the light source on a time duration required to complete the photochemical tautomerization reaction or a time duration required to complete the color change (photoisomerization).

In FIG. 10, the light source (2) can be set at an optional illumination angle (θ) with respect to a reaction part (1) (transparent container). In fact, no important influence is observed by the illumination angle (θ), since the light can pass through the container and a transmitted light can reach to a specimen of the latter is transparent, and also because the above-mentioned change to a structural isomer as a photochemical tautomer is such very rapidly that the reaction completion time is relatively short as only 150 seconds under an illuminance of even 500 lux, as is shown in FIG. 11.

If the resulting photochemical tautomer is left under a dark environment, the tautomer returns to the former state gradually after a certain period of time In the irradiation apparatus of FIG. 10, a test sample is irradiated, so that only a portion of F28 tetra-phenyl porphyrin which did not react with lithium ions is changed to the structural isomer as a photochemical tautomer. A color is changed to green when the lithium concentration in a specimen is lower than 0.5 mEq/L (=mol/L).

Figure 12:
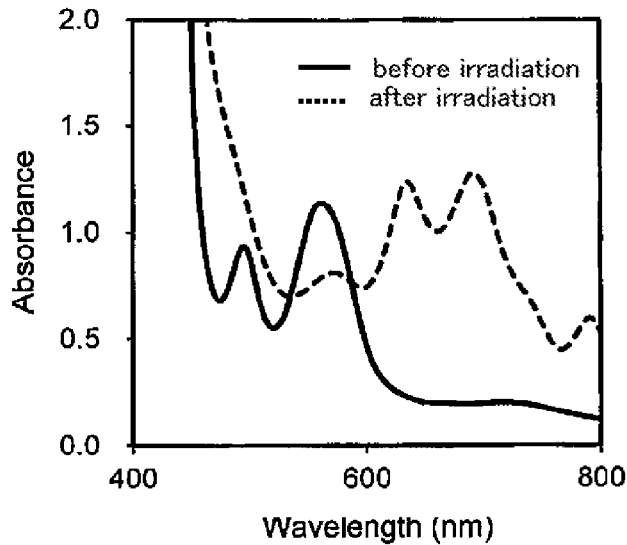
FIG. 12 A graph of electron absorption spectrum of a photochemical tautomer originated from F28 tetra-phenyl porphyrin.

FIG. 12 is a graph of electron absorption spectrum of a photochemical tautomer originated from F28 tetra-phenyl porphyrin. A solid line is an absorption spectrum in a visible light wave length range from 400 nm to 800 nm before irradiation, and a dashed line is an absorption spectrum in the same light wave length range after irradiation with the white light for about 3 minutes. This change is recognized as a change in color from yellow orange color to green color in visual observation.

Figure 13:
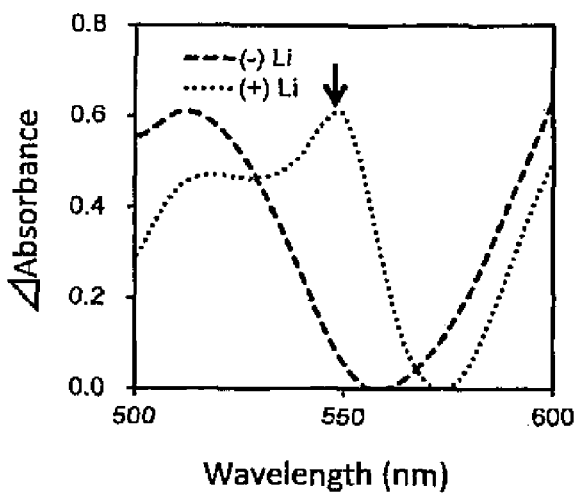
FIG. 13 A graph of the electron absorption spectrum after the F28 tetra-phenyl porphyrin complex was irradiated.

FIG. 13 is an enlarged graph of the electron absorption spectrum in a visible light range of 500 nm to 600-nm after irradiation. A thick dashed line is an absorption spectrum for the lithium ion concentration of 0.5 mEq/L (=mol/L) or less, while a fine dotted line is an absorption spectrum for the lithium ion concentration of higher than 1.5 mEq/L or more which is recognized as a red color in visual observation.

FIG. 8 shows, in [Table 3], a summary of the results of the visual judgement of the lithium concentration for control serum specimens carried out according to the principle of this invention. This result reveals that the lithium concentration in a specimen can be judged clearly by a simple and quick visual detection.

The lithium reagent compositions used in Example 1 and Example 2 were prepared by the same procedure as those described in the Patent Documents 3. In this invention, however, inventors confirmed that the lithium concentration in a specimen can be measured by naked eyes by viewing a graduation of color or a difference in color tone of a specimen. The same result as Example 1 and Example 2 were obtained in the following Example 3 also.

EXAMPLE 3

(Lithium Reagent Composition Sample 3)

| (1) First Reagent (as stabilizer and buffer solution) | | |
|---|---|---|
| Chelate agent: | Nothing | |
| Organic solvent: | Nothing | |
| Stabilizer (dispersing agent: nonionic surfactant): | TritonX-100 (®) (polyoxyethylene octylphenyl ether) | 1.0% by weight |
| Masking agent: | Triethanolamine | 10 mM |

Into a mixture of above components, 0.1M of MOPS was added to adjust pH to pH 8 and purified water was added up to the total volume of 1 liter. The resulting mixture was stored in a general-purpose preservation container.

| (2) Second Reagent (as color-development reagent) | | |
|---|---|---|
| Chelate agent: | F28 tetra-phenyl porphyrin | 0.5 g/L |
| Organic solvent: | Dimethyl sulfoxide (DMSO) | 20% by weight |
| Stabilizer (dispersing agent: nonionic surfactant): | TritonX-100(®) (polyoxyethylene octylphenyl ether) | 1.0% by weight |
| Masking agent: | Triethanolamine | 10 mM |

Into a mixture of above components, 0.05M of MOPS (buffer) was added to adjust pH to pH 7.0 and purified water was added up to the total volume of 1 liter. The resulting mixture was stored in a general-purpose preservation container.

To a measurement of lithium concentration, in the same manner as Example 1, 720 μL of the first reagent (buffer solution) and 240 μL of second reagents (color-development reagent) were added to 6 μL of a specimen and a color development reaction was carried out for a predetermined time duration.

In the same manner as Examples 1 and 2, the test sample was added to the lithium reagent composition and then the resulting mixture was irradiated with white light, so that a portion of F28 tetra-phenyl porphyrin which did not react with lithium ions was changed to a structural isomer of photochemical tautomer, resulting in that following color was developed according to the lithium concentration in the specimen:

| 0.5 mEq/L (=mol/L) or less | green color, |
|---|---|
| 0.5 mEq/L to 1.5 mEq/L | yellow color, |
| 1.5 mEq/L or more | red color. |

This color change corresponds conveniently to threshold levels of the control region and the poisoning region, so that the color change is detectable clearly by visual observation or by a colorimeter.

The above lithium reagent composition can be formed in a form of one package type of course, according to the same relationship between Example 1 and Example 2

Although the test specimen is serum in above Examples, the method according to the present invention is applicable to other specimen such as living samples including urine, blood and a plasma test sample, and also environmental sample including industrial water, drinking water and environment samples. In fact, the lithium concentration in an aqueous solution can be measured immediately by a simple colorimeter and can be evaluate by visual observation.

Characteristics of the present invention suggests such a fact that the same lithium detection method as the present invention may be applicable to another analysis reagent which can react with lithium ions such as a porphyrin compound having eight bromine atoms (Br) bonded to a pyrrole ring, for example, with expecting an influence to the electron absorption spectrum caused by light reception, although clear sharp judgement may not be expected.

The invention claimed is:

1. Method for determining the concentration of lithium by naked eyes, comprising contacting a specimen with an aqueous solution of a lithium reagent composition comprising a compound represented by following structural formula in which all hydrogens bonded to carbons of a tetraphenyl porphyrin are replaced by fluorine:

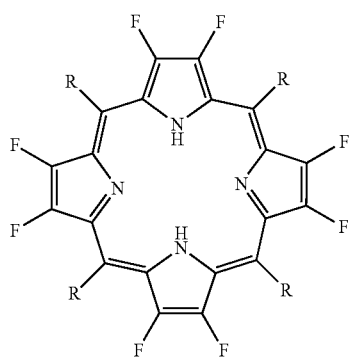

-continued

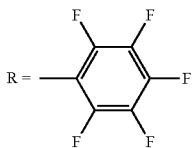

a pH regulator and a pH buffer,
irradiating the resulting solution with white light, and
observing change in color tone due to the irradiation by a visual observation to determine that the concentration of lithium is in a control range when the color changes to green, that the concentration of lithium is in a dangerous range when the color changes to red, and that the concentration of lithium is in a poisoning range when the color changes from yellow to orange before the color changes to red.

2. The method according to claim 1, wherein said change in color tone is a change from a green color which is shown when a lithium coloration complex does not exist to the final red color through a yellow color and an orange color which are shown according to an increment of an amount of the lithium coloration complex.

3. The method according to claim 2, wherein said change in color tone is produced in a range of 0.0 mM to 4.5 mM of the lithium concentration.

4. The method according to claim 1, wherein said specimen is biomaterial specimen including serum and plasma test sample.

5. The method according to claim 1, wherein said specimen is an environment sample.

* * * * *